(12) United States Patent
Frunza

(10) Patent No.: US 8,775,086 B2
(45) Date of Patent: Jul. 8, 2014

(54) LAG CALCULATION WITH CAVING CORRECTION IN OPEN HOLE

(75) Inventor: Gabriel Frunza, Balan (RO)

(73) Assignee: Weatherford/Lamb, Inc., Houston, TX (US)

( * ) Notice: Subject to any disclaimer, the term of this patent is extended or adjusted under 35 U.S.C. 154(b) by 451 days.

(21) Appl. No.: 13/076,014

(22) Filed: Mar. 30, 2011

(65) Prior Publication Data

US 2012/0253677 A1 Oct. 4, 2012

(51) Int. Cl.
*G06F 19/00* (2011.01)

(52) U.S. Cl.
USPC .......................... 702/9; 73/152.04; 73/152.42

(58) Field of Classification Search
USPC ................ 702/9; 73/152.04, 152.09, 152.42, 73/61.41; 175/40; 166/66, 255.1
See application file for complete search history.

(56) References Cited

U.S. PATENT DOCUMENTS

| 3,386,286 A | 6/1968 | Moore |
| 4,878,382 A | 11/1989 | Jones et al. |
| 2006/0113110 A1 | 6/2006 | Leuchtenberg |
| 2009/0151939 A1 | 6/2009 | Bailey et al. |

OTHER PUBLICATIONS

International Search Report and Search Opinion for PCT Application No. PCT/US2012/025844, dated May 31, 2012, 8 pages.
Whittaker, A., "Chapter 52 Mud Logging," Petroleum Engineering Handbook, Society of Petroleum Engineers, Jan. 1, 1987.

*Primary Examiner* — Jonathan C Teixeira Moffat
*Assistant Examiner* — Hien Vo
(74) *Attorney, Agent, or Firm* — Wong, Cabello, Lutsch, Rutherford & Brucculeri LLP

(57) ABSTRACT

A gas analyzer system that can detect atmospheric air gasses in drilling mud is used to calculate an actual lag time in a well. The calculated lag time and a theoretical lag time may be compared to estimate a caving percentage in an open hole section of the well.

17 Claims, 5 Drawing Sheets

LAG CALCULATION WITH CAVING CORRECTION IN OPEN HOLE

TECHNICAL FIELD

The present invention relates to the field of drilling, and in particular to a technique for improved lag time calculation.

BACKGROUND ART

Drilling operators typically need to know the time required for cuttings made by drilling operations to reach the surface, usually known as lag time. The lag period is typically either measured as a function of time or as a number of drilling fluid (frequently known as "mud") pump strokes. This has often been calculate by performing what is known as a carbide lag test, in which a small paper packet containing calcium carbide is inserted into the drill string when the Kelly is unscrewed from the pipe to make a connection. The time of the insertion of the carbide is noted, along with the pump stroke count on the mud pump. Once the connection is completed, drilling resumes. The packet is entrained in the mud and moves downhole with the mud. The mud then breaks down the paper casing, allowing the calcium carbide to react with the mud, generating acetylene gas. The gas circulates with the drilling mud downhole and back up the annulus of the well, until it reaches the surface. The acetylene can then be detected at the gas trap of the mud system, causing a peak or spike in gas readings for acetylene. The time and pump stroke count corresponding to the peak may then be noted again, and a lag interval calculated.

Carbide tests require assistance from the rig crew, and introduce time, technical, and safety issues, thus are generally not performed at every connection of drill pipe to the drill string. In some areas, carbide tests are regulated or even prohibited because of those technical and safety issues.

Certain conditions in a well, however, may affect the accuracy of a lag time calculation. One of these conditions is caving.

When drilling a well, sections of the well may be enclosed in casing, but other sections, known as open hole sections, have no casing, either because the well is being drilled without casing or because the casing has not yet been run into that section of the well. Open hole drilling is frequently done in horizontal or other directional drilling operations.

While drilling an open hole section, there is a difference between the theoretical open hole and the actual one, including changes in the borehole volume caused by cavings or cuttings accumulations. This difference may significantly affect the lag time reported. In addition, a correct estimation of the open hole volume would be valuable for other rig operations, including cementing, mud displacements, hydraulics, etc.

BRIEF DESCRIPTION OF DRAWINGS

The accompanying drawings, which are incorporated in and constitute a part of this specification, illustrate an implementation of apparatus and methods consistent with the present invention and, together with the detailed description, serve to explain advantages and principles consistent with the invention. In the drawings.

DESCRIPTION OF EMBODIMENTS

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts or suffixes are understood to reference all instance of subscripts and suffixes corresponding to the referenced number. Moreover, the language used in this disclosure has been principally selected for readability and instructional purposes, and may not have been selected to delineate or circumscribe the inventive subject matter, resort to the claims being necessary to determine such inventive subject matter. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

Recently, at least one gas analysis system, the GC-TRACER™ system available from the assignee of the current application, has allowed testing for gasses such as nitrogen, a natural component of atmospheric air. Because nitrogen (unlike carbon dioxide and oxygen, other major components of atmospheric air) does not react with typical mud additives, and is contained in such quantity in atmospheric air (78% of air by volume), nitrogen makes a useful replacement marker to use in performing lag time tests.

Figure 1:
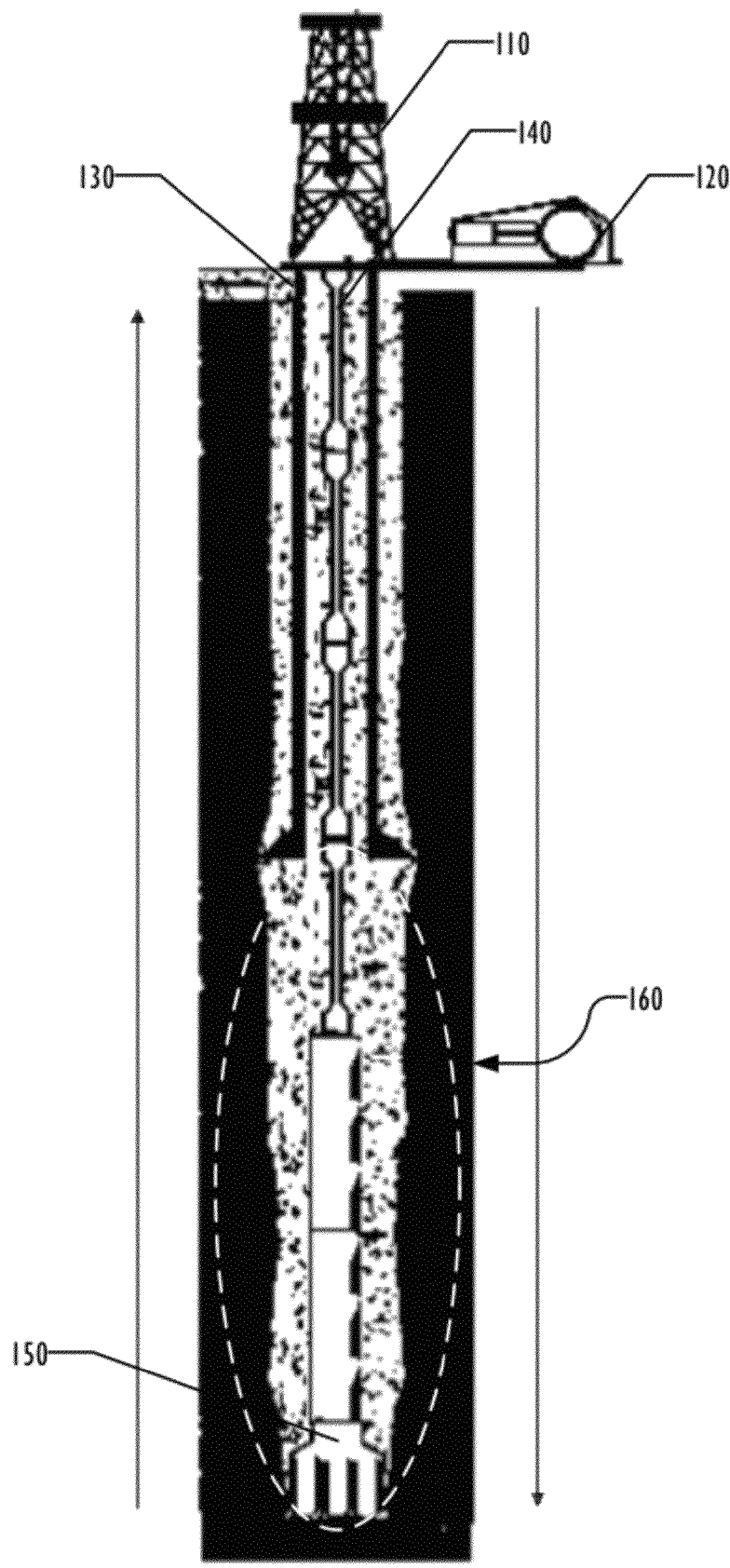
FIG. 1 is an elevation view of a typical drilling well, illustrating an open hole section that can be estimated according to one embodiment.

FIG. 1 is an elevation view of a well illustrating an open hole section that can be estimated according to one embodiment. As is well known, atmospheric air comprises a mixture of gasses, of which approximately 78% by volume is nitrogen ($N_2$) gas. In this example, a drilling rig 110 is drilling a well, and mud pump 120 is pumping drilling fluid or mud into the well, down drill string 140 to the drilling bit 150. The mud returns up the annulus and is extracted through flow lines at the bell nipple (not shown) to be reconditioned and reused. At some point, the returned mud passes through a gas trap, into which a probe of a gas analyzer system is inserted to detect and measure gas contained in the mud. This gas analyzer system (not shown) can then use the gas measurements and timings to calculate values such as the lag time and other useful data.

An upper section 130 of the well is enclosed in well casing that has been run into the borehole. A lower section 160 of the borehole has no casing, and is known as an open hole section. Because lag time is defined as the amount of time required for fluid to return uphole from the drill bit 150, sometimes measured in terms of numbers of strokes of the mud pump 120. Traditionally, the lag time is calculated based on the capacity of the mud pump and the theoretical volumes of the borehole, calculated by knowing the size of the drill bit, the volume of the drilling pipe, etc. The lag time may be measured occasionally using carbide tests or by the introduction of a detectable solid substance such as rice or lentils into the drilling mud, and measuring the time required to detect the substance in the returned drilling mud.

The volume of the open hole section 160 therefore affects that calculation directly. If the open hole section 160 is larger than the theoretical volume, lag time calculations will underestimate the real lag time. If the open hole section 160 is smaller than expected, lag time calculations based on theoretical volumes will overestimate the real lag time. As indicated above, occasional tests may be performed to calibrate the calculated lag time, but those tests involve the assistance of rig crews and incur safety risks, thus are not performed at every connection event.

By using a gas analyzer system that can detect atmospheric gas entrained in the mud during a connection, a correction can be made to the lag time calculated on theoretical volumes, without incurring the risks and operational delays or disruptions caused by carbide or solids tests. Instead of depending on theoretical calculations with occasional corrections, a new calculation according to one embodiment can directly measure an actual lag time at every connection event. Furthermore, embodiments described herein can estimate the caving percentage of the open hole section 160, providing other useful information to rig operators.

Nitrogen gas is preferable for the measurement task because if it so plentiful in atmospheric air, and is generally non-reactive to the drilling mud and additives. Although carbon dioxide ($CO_2$) and oxygen ($O_2$) are also plentiful in air, they tend to have a high reactivity to the drilling mud, especially the additives used to condition the mud, and in the case of $O_2$, also tend to be reactive to other elements of the rig, such as rusting of metals, thus may be less desirable for the measurement task.

Because $N_2$ generally has a low reactivity with drilling muds, whether water based, oil based, or synthetic, it makes a good marker for lag correction and caving percentage estimation while drilling. Because the $N_2$ source is atmospheric air, no assistance from the rig crew or extra equipment is needed for performing the measurement and calculations. Indeed, the rig crew need not even know that the calculations are being performed, unlike conventional techniques that use carbide tests, for example.

Although the following description is written in terms of $N_2$ gas, other atmospheric gasses may be used. In addition, other embodiments may use special purposes gasses that are introduced into the mud system of the drilling rig 100, typically by injecting the gas into the drilling mud prior to being pumped into the well by the mud pump 120.

Figure 2:
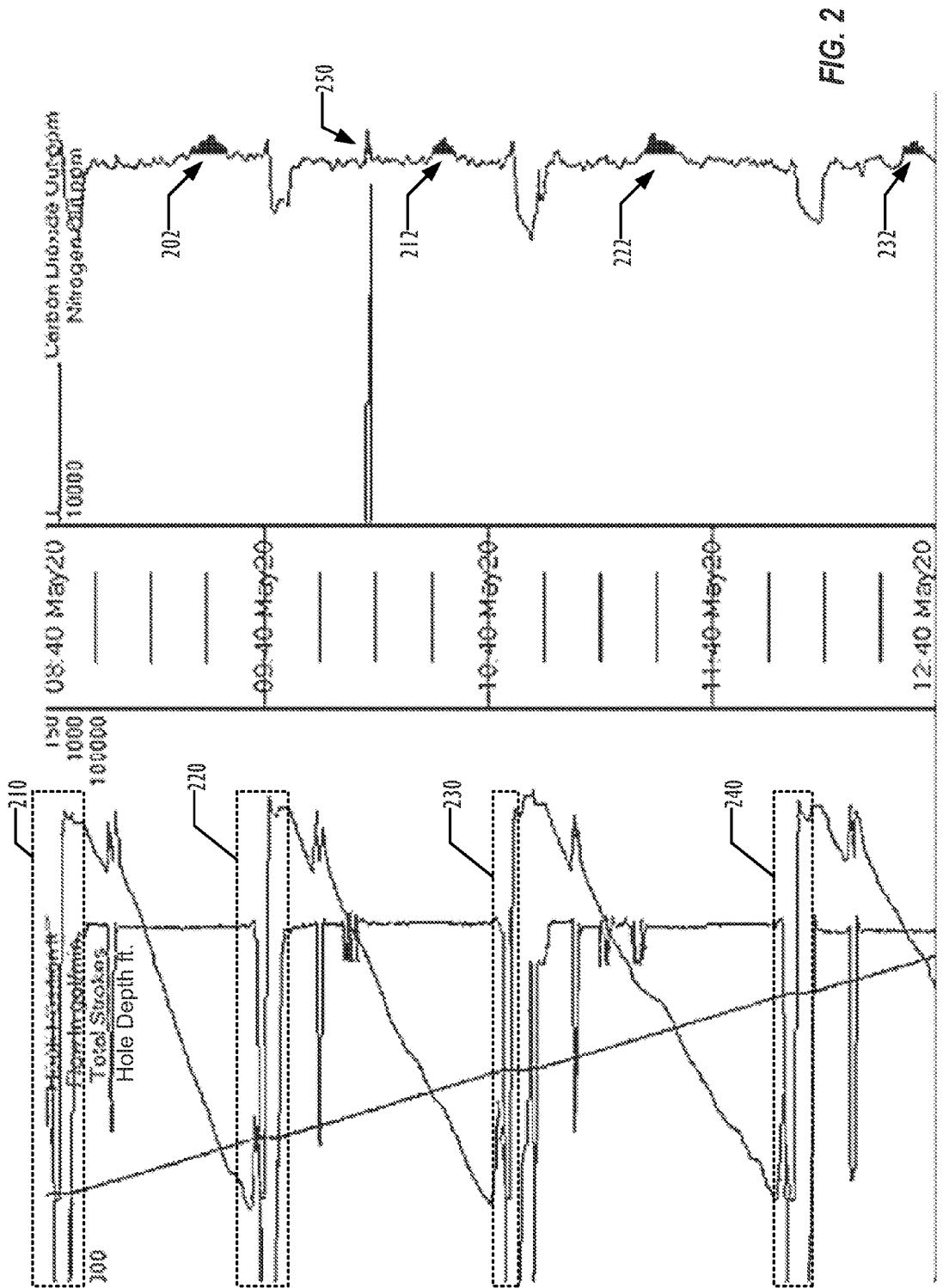
FIG. 2 is a sample log produced by a gas analyzer according to one embodiment.

FIG. 2 is a sample log from a gas analyzer system according to one embodiment that is capable of detecting and measuring nitrogen gas in drilling mud. On the left side is a graph of several measurements, including hook position, mud flow rate, total mud pump strokes, and hold depth. As illustrated in FIG. 2, four connections 210, 220, 230, and 240 are visible in the graph, indicating times when another section of pipe was added to the drill string.

On the right side of FIG. 2 are graphs of $CO_2$ and $N_2$, in parts per million (ppm) concentrations in the drilling mud as detected by the gas analyzer probe in the returned drilling mud. A trained analyst can recognize that the $N_2$ value is easily observed after each connection by the increment of the $N_2$ value by as much as 2 times or more. In this sample log graph, $N_2$ peak 202 is detecting nitrogen from a connection prior to connection 210. Peak 250 can be recognized as an event in which the gas analyzer probe is taken out of the mud system for cleaning, causing an increment in both the $N_2$ and $CO_2$ graphs. Peak 212 corresponds to connection 210, peak 222 corresponds to connection 220, and peak 232 corresponds to connection 230. The corresponding peak for connection 240 is outside the bounds of the sample graph illustrated in FIG. 2. In this sample log, the peak 212 corresponding to connection 210 comes after the connection 220 event, because of the hole depth and high rate of penetration (ROP) in this well. In other wells with a lesser hold depth or ROP, the peak corresponding to a connection may come before the next connection.

Thus, in one embodiment, lag time may be calculated using the following equation:

$$L=(N-C)-D$$

where L is the calculated lag time in units of strokes of the mud pump 120, N is the number of total mud pump 120 strokes recorded at the beginning of the $N_2$ peak, C is the number of total mud pump 120 strokes recorded at the end of the connection, and D is the number of down strokes of the mud pump 120.

This calculation may be performed after each connection, correcting the lag time estimate made based on theoretical volumes. In one embodiment, the gas analyzer may store the calculated lag time in a database, providing a record of the evolution of lag time through the drilling of the well, typically associating the lag time with a depth of the well.

Although the above calculations are set forth in terms of mud pump strokes, other units may be employed, including volume and time.

Figure 3:
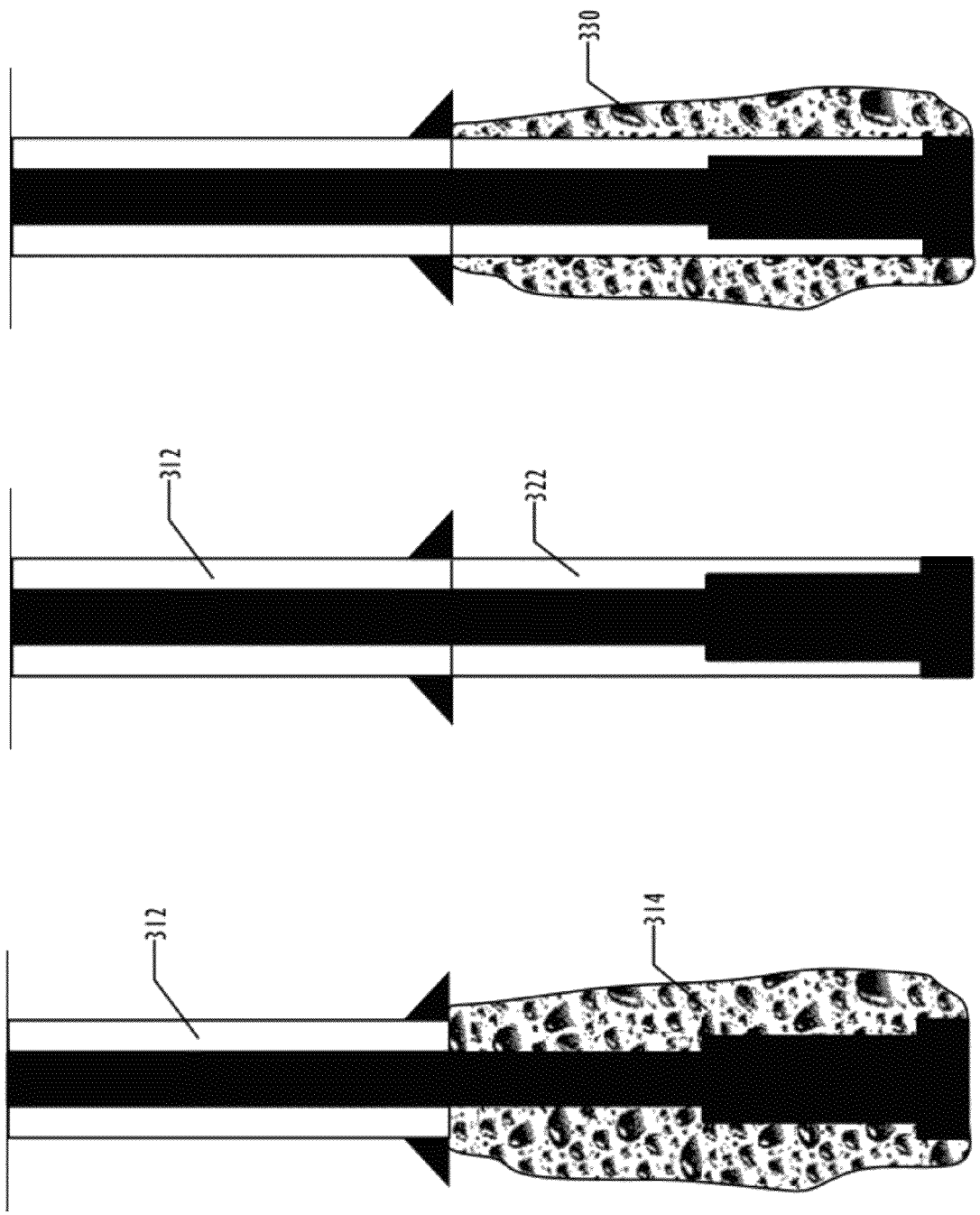
FIG. 3 is a diagram illustrating a technique for calculating a caving percentage according to one embodiment.

A second calculation of caving may also be facilitated by a system that employs the calculations above, as illustrated in FIG. 3. By comparing the lag time in strokes calculated from the $N_2$ peaks using the formula set forth above with the lag time in strokes calculated from the theoretical volume of the well and mud pump capacity, a caving amount (330) may be calculated. As illustrated in FIG. 3, the calculated lag time corresponds to a volume that includes the volume of the casing and drill pipe annulus (312) plus the volume of the borehole and drill string annulus (314). The theoretical lag time corresponds to the volume of the casing and drill pipe annulus (312) plus the volume of the nominal borehole and drill string annulus. The comparison of those two values thus corresponds to the excess volume of the borehole (330). (Or, in cases of a decreased borehole volume, such as may be caused by salt flow or gumbo shale encroachment, the less than expected volume.) In one embodiment, this can be calculated as a percentage according to the following formula:

$$Caving\%=(Theoretical\ Lag*100)/(Calculated\ Lag)-100$$

In one embodiment, the caving percentage may be calculated every connection and recorded in a depth database with the calculated lag time, allowing caving evolution to be recorded and plotted or otherwise displayed or reported over the drilling of the well. The caving percentage may be positive (indicating a larger hole than the theoretical calculation), or negative (indicating a smaller hole than the theoretical calculation). Knowledge of the caving percentage is useful to drilling engineers. For example if the open hole section 160 is significantly enlarged, then drilling engineers are preferably advised of that situation, because drilling rig hydraulics may no longer be optimized, causing problems that may include excessive torque, drag, or stuck pipe. In addition, knowledge of open hole section 160 volume changes may be important for other types of operations, such as cementing.

Each measurement of lag time provides an opportunity to calculate the incremental change in average borehole size and caving % versus depth and versus time. Time-dependent changes and/or depth-dependent changes may be correlated with the geology, wellbore geometry, and data concerning the wellbore, indigenous fluids and drilling parameters obtained from other surface and downhole measurements.

As the data emerges while drilling progresses, a trend of borehole caving characteristics may be established. For example, at a given drilling depth of x, an actual lag time of y is measured, resulting in a calculated caving % of z. Then at the next data point (depth x+a), a theoretical lag time would be y+b (based upon the nominal borehole diameter), but may be measured to be y+c, where c>b. This means the actual borehole volume has increased by more than the anticipated amount for the given bit size and incremental length drilled. This incremental increase in lag time above the theoretical increment directly relates to an incremental increase of average borehole size over nominal size. Successive measurements and similar calculations will reveal any trend in the data. For example, the deviation from theoretical values may be constant over time or depth, or this deviation may start as a small value but suddenly increases at a specific location or time.

Such changes in the characteristics of caving over time may be due to one or more of several factors. For example, the interaction between certain rock types (for example, shales) and mud systems (for example, water-based muds) may result in increasing caving from exposed rock after a particular length of time of exposure. Data from logging while drilling (LWD) sensors (for example, resistivity, sonic, etc.) and/or cuttings may be used to confirm that caving is occurring from rock higher in the borehole than the current depth.

An incremental change in the characteristics of caving versus depth may occur when drilling through a boundary from one rock type into another. Again, data from other sources (LWD, cuttings, hydrocarbon detection, drilling ROP, etc.) may be correlated with the lag time, borehole volume, and average borehole size calculations to indicate the nature of the borehole.

Significant changes in wellbore trajectory may cause sloughing of material off the borehole wall at one or more downhole locations in the borehole due to abrasion with drillpipe. In an extreme case, this may lead to the known phenomenon of "key-seating." This increase in borehole volume beyond the nominal borehole size would be detected through the lag time and caving % calculation, but the location of this sloughing may be determined through the nature of the cuttings being circulated to surface and/or through LWD data. For example, a sonic caliper measurement may indicate that the fresh hole being drilled is roughly equal to the nominal size of the borehole (the bit diameter), but if the incremental lag time and caving % calculations indicate significant borehole enlargement, then it can be deduced that the enlargement is occurring at a shallower depth than the drill bit and drilling bottom hole assembly (BHA). Further examination of the cuttings and other surface logging data (hydrocarbon ratios, etc.) may further indicate the location (depth) where the measured borehole enlargement is occurring.

Additionally, if significant or potentially troublesome borehole enlargement is suspected to have occurred at one or more downhole locations, then further correlation data may be obtained by performing a circulation and lag time check at appropriate downhole locations while a drill string is being retrieved out of the borehole. This would provide further measurements of incremental borehole size (and volume) versus depth, which would be particularly important information for any subsequent operations, such as fluid sampling, casing running and cementing. Additionally, by comparing these measurements while retrieving the drilling assembly to those measurements obtained while drilling, a correlation may be developed of how the borehole enlargement occurred versus time and/or versus depth, plus the identification of specific downhole locations where the measured enlargement occurred.

All the above information and correlation with other data acquired at the wellsite may be of use to develop different mud systems and/or recommended well designs and/or drilling practices for future drilling activities in the same or similar geology and/or environments.

Figure 4:
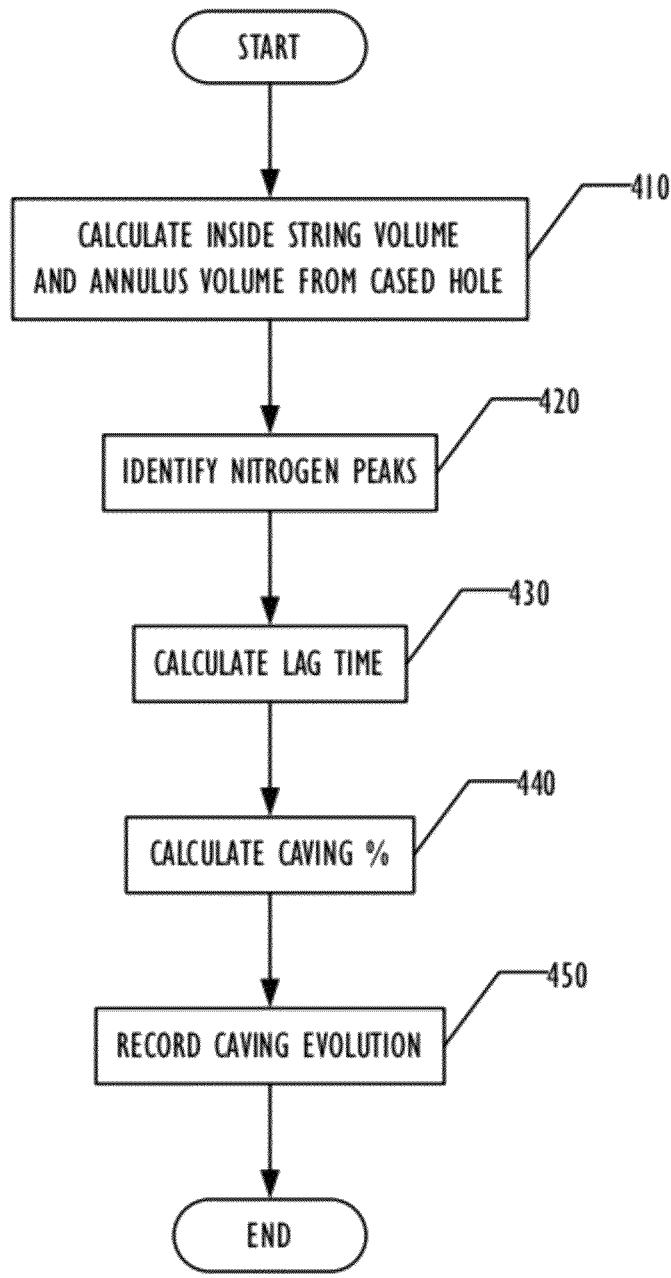
FIG. 4 is a flowchart illustrating a technique for performing lag calculation and caving percentage according to one embodiment.

FIG. 4 is a flowchart illustrating a technique for calculating lag time and caving percentage according to one embodiment. In block 410, theoretical calculations of an inside drill string volume and annulus volume of the cased hole are calculated. In block 420, $N_2$ peaks are detected by the gas analyzer unit, and correlated with connections. Then, in block 430, the lag time for the well may be calculated using the formula set forth above. In addition, the lag time for the well may be calculated using the theoretical values determined in block 410. In block 440, the caving percentage may be calculated by comparing the actual measured lag time and the theoretical lag time calculated in block 430. In block 450, embodiments may record the caving evolution of the well in a database by well depth or other desired measure. Other calculations may be performed as desired, and other data may be collected by the gas analyzer as desired.

Figure 5:
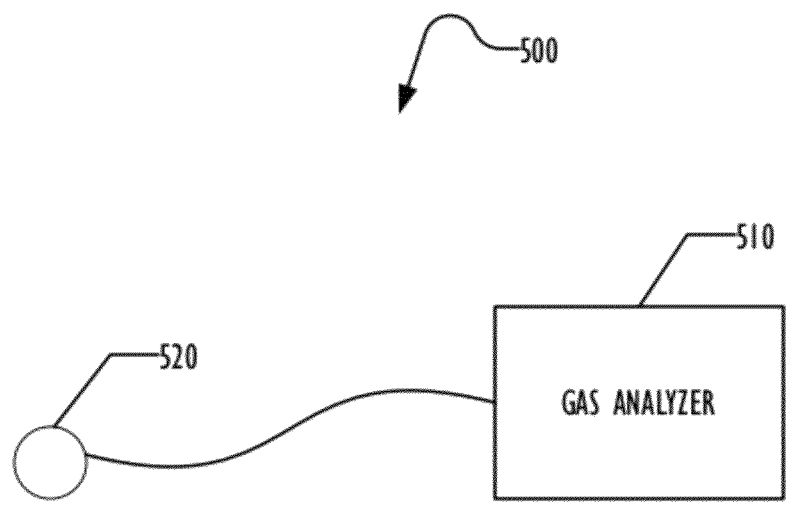
FIG. 5 is a block diagram illustrating a gas analyzer system capable of performing the techniques described herein according to one embodiment.

FIG. 5 is a block diagram illustrating a gas analyzer system 500 according to one embodiment that can perform the calculations set forth above. A probe 520 is connected to a gas analyzer system unit 510. The probe 520 is operationally immersed in the drilling mud, typically in a gas trap disposed near the shale shakers in the mud return system. The probe 520 is preferably capable of detecting and measuring $N_2$ gas and sends signals to the gas analyzer system unit 510 for logging and reporting. The gas analyzer system unit 510 may be comprised of various elements, including computational elements, that can evaluate and analyze readings from the probe 520 and possibly other data sources. An example of such a gas analyzer system 500 is the GC TRACER™ system available from the assignee of the present application. Such systems are known in the art, and are not further described herein.

Interpretative software may be provided for execution by a processor contained in the gas analyzer system unit 510 to perform the calculations described above. In some embodiments, the interpretative software may detect the occurrences of the connections and the peaks in the N2 gas automatically; in other embodiments, an analyst may review graphical or numeric output from the software and indicate the presence of the connections and peaks, triggering the calculation by such indication. The software may be provided to the gas analyzer system unit on a non-volatile machine-readable storage media known to the art, including, but not limited to, all forms of optical and magnetic, including solid-state, storage elements, including removable media, and may be included within gas analyzer system unit 510 or be external to gas analyzer system unit 510. In some embodiments, analysis data generated by the gas analyzer system unit 510 may be stored in a database stored on a storage device included within gas analyzer system unit 510 or external to gas analyzer system unit 510.

It is to be understood that the above description is intended to be illustrative, and not restrictive. For example, the above-described embodiments may be used in combination with each other. Many other embodiments will be apparent to those of skill in the art upon reviewing the above description. The scope of the invention therefore should be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A method of estimating an amount of caving in an open hole drilling well, comprising:
   calculating by a gas analyzer system an actual lag for a well by detecting a predetermined component of atmospheric air in a drilling fluid with a gas analyzer probe, comprising:
      detecting a connection event;
      detecting a change in an amount of the predetermined component of atmospheric air in the drilling fluid corresponding to the connection event;
      determining a first quantity of mud pump strokes at an end of the connection event;
      determining a second quantity of mud pump strokes at a beginning of the change in the amount of the predetermined component of atmospheric air in the drilling fluid corresponding to the connection event;
      determining a third quantity of down strokes of the mud pump; and
      calculating the actual lag by subtracting the second quantity and the third quantity from the first quantity;
   calculating by the gas analyzer system a theoretical lag for the well; and
   calculating by the gas analyzer system a caving amount by comparing the actual lag and the theoretical lag.

2. The method of claim 1, wherein the component of atmospheric air is nitrogen gas.

3. The method of claim 1, repeating the acts of calculating an actual lag, calculating a theoretical lag, and calculating a caving amount for a plurality of connection events.

4. The method of claim 3, further comprising:
   calculating a trend in a borehole caving over time.

5. The method of claim 3, further comprising:
   calculating a trend in a borehole caving corresponding to location.

6. The method of claim 3, further comprising:
   correlating the actual lag, theoretical lag, and caving amount for a plurality of connection events with data from other sources to indicate a state of a borehole.

7. The method of claim 3, wherein the plurality of connection events is every connection event for the well.

8. The method of claim 3, further comprising:
   identifying specific downhole locations where deviations from a nominal borehole occurred.

9. The method of claim 3, further comprising:
   storing the actual lag in a database.

10. The method of claim 3, further comprising:
    storing the caving amount in a database.

11. A gas analyzer system, comprising:
    a gas analyzer probe, configured to detect and measure a predetermined component of atmospheric air in a drilling fluid; and
    a gas analyzer system unit, coupled to the gas analyzer probe, comprising:
       a processor;
       instructions for execution by the gas analyzer system unit, comprising instructions that when executed by the processor, cause the processor to:
          calculate an actual lag for a well by detecting the predetermined component of atmospheric air in the drilling fluid, comprising instructions that when executed cause the processor to:
             detect a connection event;
             detect a change in an amount of the predetermined component of atmospheric air in the drilling fluid corresponding to the connection event;
             determine a first quantity of mud pump strokes at an end of the connection event;
             determine a second quantity of mud pump strokes at a beginning of the change in the amount of the predetermined component of atmospheric air in the drilling fluid corresponding to the connection event;
             determine a third quantity of down strokes of the mud pump; and
             calculate the actual lag by subtracting the second quantity and the third quantity from the first quantity;
          calculate a theoretical lag for the well; and
          calculate a caving amount by comparing the actual lag and the theoretical lag.

12. The gas analyzer system of claim 11, wherein the predetermined component of atmospheric air is nitrogen gas.

13. The gas analyzer system of claim 11, wherein the instructions further comprise instructions that when executed by the processor cause the processor to repeat the acts of calculating an actual lag, calculating a theoretical lag, and calculating a caving amount for a plurality of connection events.

14. The gas analyzer system of claim 13, wherein the plurality of connection events is every connection event for the well.

15. The gas analyzer system of claim 13, further comprising:
    a database, coupled to the gas analyzer system unit,
    wherein the software further comprises instructions that when executed by the processor cause the processor to:
       store the actual lag in the database.

16. The gas analyzer system of claim 13, further comprising:
    a database, coupled to the gas analyzer system unit,
    wherein the software further comprises instructions that when executed by the processor cause the processor to:
       store the caving amount in a database.

17. A non-transitory machine-readable storage media, containing instructions that when executed by a gas analyzer system unit cause the gas analyzer system unit to:
    calculate an actual lag for a well by detecting a predetermined component of atmospheric air in a drilling fluid, comprising instructions that when executed cause the gas analyzer system unit to:
    detect a connection event;
    detect a change in an amount of the predetermined component of atmospheric air in the drilling fluid corresponding to the connection event;
    determine a first quantity of mud pump strokes at an end of the connection event;
    determine a second quantity of mud pump strokes at a beginning of the change in the amount of the predetermined component of atmospheric air in the drilling fluid corresponding to the connection event;
    determine a third quantity of down strokes of the mud pump; and
    calculate the actual lag by subtracting the second quantity and the third quantity from the first quantity;
    calculate a theoretical lag for the well; and calculate a caving amount by comparing the actual lag and the theoretical lag.

* * * * *